US009237888B2

(12) United States Patent
Sengun et al.

(10) Patent No.: US 9,237,888 B2
(45) Date of Patent: Jan. 19, 2016

(54) METHODS AND DEVICES FOR THREADING SUTURES

(71) Applicant: DePuy Mitek, LLC

(72) Inventors: Mehmet Z. Sengun, Canton, MA (US); Gary McAlister, Franklin, MA (US); Gregory R. Whittaker, Raynham, MA (US); David B. Spenciner, Raynham, MA (US)

(73) Assignee: MEDOS INTERNATIONAL SARL, Le Locle (CH)

( * ) Notice: Subject to any disclaimer, the term of this patent is extended or adjusted under 35 U.S.C. 154(b) by 486 days.

(21) Appl. No.: 13/623,467

(22) Filed: Sep. 20, 2012

(65) Prior Publication Data

US 2014/0081322 A1 Mar. 20, 2014

(51) Int. Cl.
*A61B 17/04* (2006.01)
*A61B 17/00* (2006.01)
*A61B 17/06* (2006.01)
*A61B 19/00* (2006.01)

(52) U.S. Cl.
CPC .......... *A61B 17/0401* (2013.01); *A61B 17/0485* (2013.01); *A61B 2017/00004* (2013.01); *A61B 2017/0053* (2013.01); *A61B 2017/00526* (2013.01); *A61B 2017/0412* (2013.01); *A61B 2017/0414* (2013.01); *A61B 2017/0458* (2013.01); *A61B 2017/06185* (2013.01); *A61B 2019/444* (2013.01); *D10B 2509/04* (2013.01)

(58) Field of Classification Search
CPC ........... A61B 17/0401; A61B 17/0485; A61B 2017/00004; A61B 2017/0053; A61B 2017/0414; A61B 2017/06185; A61B 2017/0412; A61B 2017/00526; A61B 2017/0458; A61B 2019/444; D10B 2509/04
USPC .................................. 606/228, 232
See application file for complete search history.

(56) References Cited

U.S. PATENT DOCUMENTS

| 6,045,571 A | 4/2000 | Hill et al. |
| 6,994,719 B2 | 2/2006 | Grafton |
| 7,654,321 B2 | 2/2010 | Zazovsky et al. |

(Continued)

FOREIGN PATENT DOCUMENTS

| EP | 2 455 003 A2 | 5/2012 |
| GB | 2474866 A | 5/2011 |
| WO | WO-2006108735 A1 | 10/2006 |

OTHER PUBLICATIONS

Extended European Search Report issued in European Application No. 13185438.2 dated Jan. 20, 2014.

*Primary Examiner* — Gregory Anderson
*Assistant Examiner* — Son Dang

(57) ABSTRACT

Methods and devices are provided for anchoring suture to bone. In one embodiment, an elongate weave of fibers can be provided having a first portion with a first pick count and a second portion with a second pick count that is greater than the first pick count. The first portion can have a cross-section that deforms in response to a force that is applied thereto. The first portion can have a collapsible diameter and can have a bending stiffness that is lower than a bending stiffness of the second portion of the suture. The first portion can also have a first pattern that is different than a second pattern on the second portion of the suture. The first portion can be threaded into a suture anchor such that it can be doubled over upon itself. The present invention also provides exemplary sutures and drivers that can be used with the various methods and devices disclosed herein, or with other methods and devices known in the art.

19 Claims, 7 Drawing Sheets

(56) References Cited

U.S. PATENT DOCUMENTS

| | | |
|---|---|---|
| 8,088,146 B2 | 1/2012 | Wert et al. |
| 8,114,128 B2 | 2/2012 | Cauldwell et al. |
| 8,133,257 B2 | 3/2012 | Cook et al. |
| 2004/0010286 A1* | 1/2004 | Gieringer .................. 606/228 |
| 2004/0267362 A1* | 12/2004 | Hwang et al. ............ 623/13.15 |
| 2009/0076544 A1 | 3/2009 | DiMatteo et al. |
| 2010/0093258 A1 | 4/2010 | Glenn et al. |
| 2012/0197294 A1 | 8/2012 | Martin |

\* cited by examiner

FIG. 1
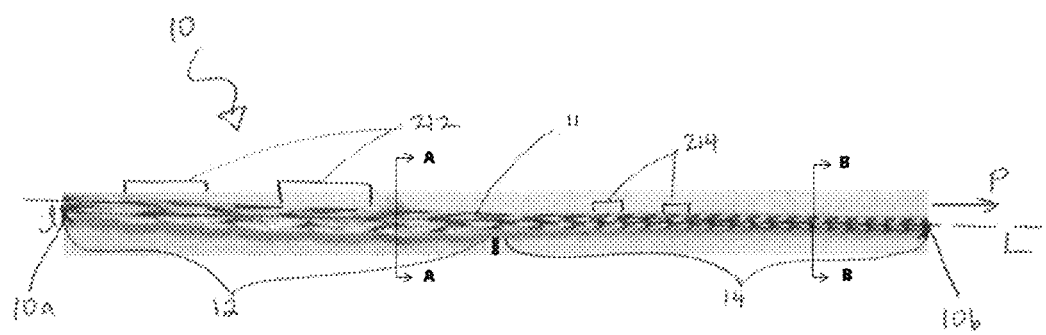
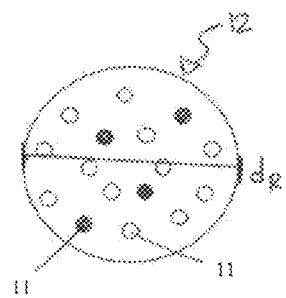
FIG. 2A
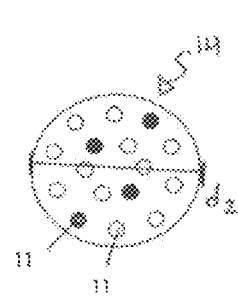
FIG. 2B
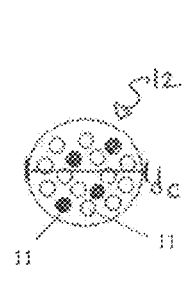
FIG. 2C
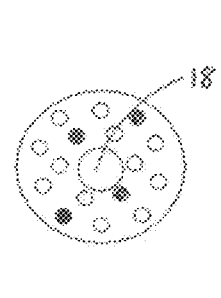
FIG. 2D

METHODS AND DEVICES FOR THREADING SUTURES

FIELD OF THE INVENTION

The present invention relates generally to sutures and to methods and devices for threading sutures into suture anchors.

BACKGROUND OF THE INVENTION

The complete or partial detachment of ligaments, tendons and/or other soft tissues from their associated bones within the body are relatively commonplace injuries, particularly among athletes. Such injuries are generally the result of excessive stresses being placed on these tissues. By way of example, tissue detachment may occur as the result of an accident such as a fall, over-exertion during a work-related activity, during the course of an athletic event, or in any one of many other situations and/or activities. In the case of a partial detachment, the injury will frequently heal itself, if given sufficient time and if care is taken not to expose the injury to further undue stress. In the case of complete detachment, however, surgery may be needed to re-attach the soft tissue to its associated bone or bones.

Numerous devices are currently available to re-attach soft tissue to bone. Examples of such currently-available devices include screws, staples, suture anchors, and tacks. In soft tissue re-attachment procedures utilizing screws, the detached soft tissue is typically moved back into its original position over the bone. Then the screw is screwed through the soft tissue and into the bone, with the shank and head of the screw holding the soft tissue to the bone. Similarly, in soft tissue re-attachment procedures utilizing staples, the detached soft tissue is typically moved back into its original position over the bone. Then the staple is driven through the soft tissue and into the bone, with the legs and bridge of the staple holding the soft tissue to the bone.

In soft tissue re-attachment procedures utilizing suture anchors, an anchor-receiving hole is generally first drilled in the bone at the desired point of tissue re-attachment. A suture anchor is then deployed in the hole using an appropriate installation tool. This effectively locks the suture, with soft tissue attached thereto.

While suture anchors provide an effective, minimally-invasive technique for soft tissue repair, it is desirable to utilize an anchor having a small diameter so as to avoid unnecessary trauma. The size of the anchor, however, can be limited by the size of the suture. Typically, a single strand of repair suture is folded and trailing ends of the suture are attached to a threader loop, which is used to pull the folded suture into the anchor. When a folded suture is used, the cannulated portion of the anchor must typically be large enough to accommodate at least four times the thickness of the repair suture. This in turn restricts the ability to reduce the size of the anchor.

Accordingly, there remains a need for improved methods and devices for attaching soft tissue to bone.

SUMMARY OF THE INVENTION

Various surgical devices and methods are provided herein. In one embodiment, a suture is provided that includes a biocompatible weave of fibers having a first length with a first pick count and a second length with a second pick count. The first length can have a cross-section that is configured to deform when a force is applied thereto. In some embodiments, the first length can have a resting outer diameter that is greater than an outer diameter of the second length. The first length can be configured to collapse in diameter when a force is applied thereto. The first length can include a terminal end portion of the suture. In some embodiments, the elongate weave can include a hollow lumen extending at least partially therethrough. The weave of fibers can also include varying patterns along the length thereof, such as at least one strand having a first color and at least one additional strand having a second color that differs from the first color such that the first length defines a first pattern and the second length defines a second pattern that differs from the first pattern.

The suture can vary in a number of ways. The second length can have a bending stiffness that is greater than a bending stiffness of the first length. In some embodiments, the collapsed outer diameter of the first length can be less than or approximately equal to the outer diameter of the second length. In some embodiments, the pick count of the second length can be about 60 picks per inch. In other aspects, the first and second patterns can each include an uninterrupted series of repeating units. The repeating unit on the first pattern can have a length that is greater than a length of the repeating unit of the second pattern.

A surgical kit is also provided and can include a biocompatible elongate weave of fibers having a first length with a first pick count and a second length with a second pick count that is greater than the first pick count. The first length can have a cross-section that can be configured to deform when a force is applied thereto. The kit can also include a cannulated anchor having an inner lumen configured to receive the weave of fibers. In some embodiments the inner lumen can be configured to receive a doubled over portion of the first length of the weave of fibers. In some embodiments the surgical kit can include a threader tab configured to pull the weave of fibers into the inner lumen of the cannulated anchor. In some embodiments, the kit can also include at least one additional biocompatible elongate weave of fibers.

Methods for threading a suture into a suture anchor are also provided. In one embodiment, the method can include threading a first portion of a suture into a cannulated anchor such that the first portion of the suture is doubled over upon itself, and such that a second portion of the suture extends from the cannulated anchor. The first portion of the suture can have a pick count that is less than a pick count of the second portion of the suture. In certain aspects, the first portion of the suture can define a first pattern extending therealong, and the second portion of the suture can define a second pattern extending therealong that differs from the first pattern such that the first portion indicates a portion of the suture to be threaded into the cannulated anchor as a double strand.

The surgical method can include a variety of modifications. For example, the method can include pulling the first portion of the suture into the cannulated anchor with a threader tab. The first portion of the suture can have a resting cross-section, and the method can further include pulling the first portion of the suture through the cannulated anchor such that the cross-section of the first portion of the suture deforms. The suture can be wrapped around a suture-receiving member extending across an inner lumen of the suture anchor such that the suture is coupled to the suture anchor. In some embodiments, the first portion can include first and second legs of the suture, where the suture includes a mid-portion between the first and second legs. In some aspects, the method can include implanting the suture anchor in bone and securing the terminal ends of the suture such that tissue attached to the suture is securely anchored to the bone.

BRIEF DESCRIPTION OF THE DRAWINGS

The invention will be more fully understood from the following detailed description taken in conjunction with the accompanying drawings, in which:

FIG. 1 is a perspective view of one embodiment of a suture having first and second portions with different pick counts;

FIG. 2A is a cross-sectional view of the first portion of the suture of FIG. 1 taken along line A-A;

FIG. 2B is a cross-sectional view of the second portion of the suture of FIG. 1 taken along B-B;

FIG. 2C is a cross-sectional view of the first portion of the suture of FIG. 1 in a tensioned state;

FIG. 2D is a cross-sectional view of an embodiment of a suture with a hollow channel extending therethrough;

DETAILED DESCRIPTION OF THE INVENTION

Figure 4:
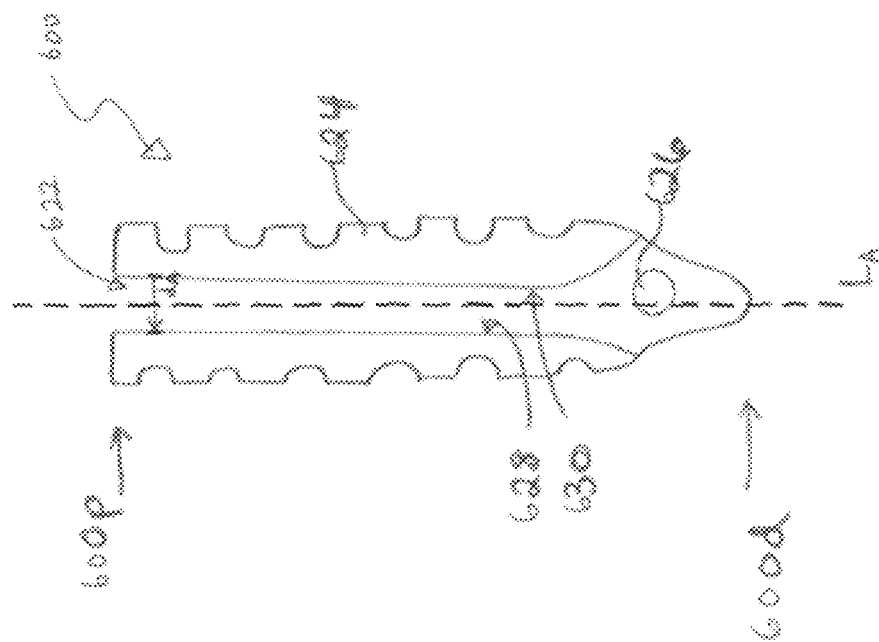
FIG. 4 is a cross-sectional view of one embodiment of a suture anchor.

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Various devices and methods are provided for anchoring suture to bone. In an exemplary embodiment, a suture is provided and is formed from several fibers or filaments that are woven together. In general, the suture can have distinct portions along a length thereof that each have a specific pick count. The pick count, or PPI, refers to the setting used during manufacture to define the number of picks (i.e., the number of times the fibers cross) per inch of material. The pick count can affect the tightness or looseness of the weave, as well as the dimensions and the mechanical properties of the suture. The mechanical properties important for surgical applications include strength, fatigue, resistance to abrasion, resistance to nicking, stiffness, and knot holding capability. Therefore, the pick count is carefully chosen to optimize these parameters. For example, a pick count that is too high can lead to premature loosening of the knot, whereas a pick count that is too low can cause the suture to be easily damaged by surgical instruments. The pick count for ORTHOCORD® #2 (manufactured by DePuy Mitek), for example, is chosen to be around 60 PPI to deliver an overall optimized performance. However, 60 PPI may not render the best results for the suture's ability to fit into and around tight passages, for which a looser suture structure provided by a lower pick count may be a better choice. Therefore, it may be beneficial for a suture to have multiple portions with different pick counts to independently address these conflicting requirements.

In one embodiment, the suture can include a first length or portion having a first pick count and a second length or portion having a second pick count that is greater than the first pick count. As a result of the smaller pick count of the first portion, the fibers will be more loosely woven than the fibers of the second portion. The first portion can thus be configured to deform or collapse more easily when a force is applied to the suture, such as an axial force, a compression force, a bending force, or a pulling force, for example. The first portion can also be more flexible than the second portion because of the looser weave given by the lower pick count, and as a result the first portion can have a bending stiffness that is lower than a bending stiffness of the second portion. Such a configuration will allow the fibers of the first portion to realign relative to one another when the first portion is deformed. For example, the first portion can be folded or bent, and the fibers will reposition at the bend to allow the first portion to deform and change in cross-sectional shape. This will allow the first portion to be more easily introduced into a smaller diameter suture anchor, as compared to a folded portion of suture having a high pick count that retains a relatively circularly cross-sectional shape when bent. As mentioned above, however, the tissue repair can be accomplished with the higher pick-count portion of the suture, which is optimized for that purpose. In some embodiments, the suture can have three or more portions having differing pick counts. The suture can also include tactile and/or visual indicators for distinguishing the different portions. For example, some of the filaments in the suture can be colored such that weaving the filaments creates a pattern of repeating units on the suture. In certain aspects, the first portion can have a first pattern that is different than a second pattern on the second portion.

While the suture can be used in a variety of applications, in one exemplary embodiment the suture is particularly useful with bone anchors for soft tissue repair. As a result of the differing pick counts along the length of the suture, the flexible low pick count portion of the suture can allow for use with a cannulated suture anchor having a small-diameter inner lumen. For example, the first portion of the suture having the lower pick count can be threaded into a suture anchor such that the second portion extends from the suture anchor. In some embodiments, the first portion can be doubled over upon itself. The doubled over portion can be passed through a lumen of the anchor, passed around a suture-receiving member, and passed back through the lumen of the anchor such that four lengths of the suture extend through the lumen. In other embodiments, a different number of lengths of the suture, such as two, can extend through the lumen of the anchor. In some other embodiments, eight lengths of suture may coexist in the lumen of the anchor, especially while the sutures are being coupled to the anchor. Where multiple lengths of suture extend through the anchor, the flexible low pick count portion of the suture can be particularly advantageous as it allows the lumen's diameter to remain relatively small and yet still be capable of slidably receiving the suture therein. The second high pick count portion of the suture can optionally remain partially or entirely outside of the anchor, and can couple to tissue to securely attach the tissue to the suture anchor, and thus to bone. In some embodiments, a threader tab can be used to pull the suture into the suture anchor. The present invention also provides exemplary sutures that can be used with the various methods and devices disclosed herein, or with other methods and devices known in the art. A person skilled in the art will appreciate that, while methods and devices are disclosed herein for anchoring soft tissue to bone, the methods and devices can be used in a variety of other medical procedures.

FIG. 1 illustrates one exemplary embodiment of a suture 10 with varied pick counts. The suture 10 is formed from an elongate weave of fibers or filaments 11, and the suture 10 has first and second terminal ends 10a, 10b and a length l extending therebetween along a longitudinal axis L. The pick count can vary along the length of the suture to define distinct portions that differ in flexibility. The suture can have a number of different portions along its length. As shown in FIG. 1, the suture 10 includes a first portion 12 that has a pick count that is less than a pick count of a second portion 14.

While the suture 10 shown in FIG. 1 is formed from sixteen filaments 11, the suture can be formed from any number of filaments. Preferably, the number of filaments in the suture is in the range of 4 to 32, and more preferably in the range of 8 to 16 depending on the particular surgical procedure to be performed. The diameter, material, and color of each filament can also vary. Generally, each filament can be formed from a biocompatible material that can be absorbable or non-absorbable. Suitable materials include, but are not limited to, polyethylene, including ultra-high molecular weight polyethylene, polyester, polypropylene, PDS, PLA, PGA, and blends or mixtures of any of the preceding. A suture can be formed from identical filaments, or alternatively, the suture can be formed from filaments with varying diameters, materials, and/or colors. FIG. 1 shows a suture 10 formed of filaments 11 made of different materials and having different colors. Variations in the number of filaments and in the properties of the filaments can provide different patterns on the suture, as discussed further below.

The filaments can be braided, twisted, or woven together in a number of different configurations to form the suture. For ease of reference, the phrases "weave" or "weave of fibers" will be used to describe the suture regardless of whether the filaments are woven, twisted, or braided together. The number of filaments, the direction or orientation of each filament, and/or the pick count can vary. A pick count or picks per inch (PPI) represents the number of times the fibers cross for every inch of length of the suture. A lower pick count will result in a suture having a relatively loose weave, while a higher pick count will result in a suture having a relatively tight weave. The pick count can vary over the length of the suture. In one exemplary embodiment, as shown in FIG. 1, the pick count of the first portion 12 can be about 15 PPI and the pick count of the second portion 14 can be about 60 PPI. A person skilled in the art will appreciate that the pick count can vary. By way of non-limiting example, the pick count can be in the range of about 10 PPI to 100 PPI, and more preferably can be in the range of about 15 PPI to 60 PPI. The pick count can be selected based on various factors, such as the type of filaments used, and/or the type of surgical procedure to be performed. As indicated above, the pick count can affect the tightness of the weave and mechanical properties of the suture. As shown in FIG. 1, for example, the first portion 12 of the suture 10 is more loosely woven than the second portion 14 of the suture 10.

The pick count can also affect a cross-section or an average outer diameter of the suture. Suture size is typically determined by an average outer diameter of a cross-section of the suture, according to standards determined by the United States Pharmacopeia (USP). As shown in FIGS. 2A and 2B, a resting outer diameter $d_R$ of the first length 12 with the lower pick count taken along the line A-A of FIG. 1 can be greater than a resting outer diameter $d_2$ of the second length 14 that has a higher pick count taken along the line B-B of FIG. 1. However, the resting diameter $d_R$ of the first length 12 can include adjustable spaces between the filaments 11. The adjustable spaces between the filaments can be reduced or removed by various forces, such as pulling the suture, compressing the suture, etc. For example, when an axial pulling force P is applied to the suture 10 in the direction shown in FIG. 1, the filaments 11 can align themselves within the adjustable spaces such that the resting diameter $d_R$ of the first portion, as shown in FIG. 2A, reduces to the collapsed outer diameter $d_C$ of the first portion, as shown in FIG. 2C. Alternatively, or in addition, the filaments can align themselves such that a cross-section of the suture changes in shape. For example, the filaments can align themselves such that a cross-section of one or more lengths of the suture conforms to a cross-sectional shape of a lumen that they may be in. The collapsed outer diameter $d_C$ can be less than the outer diameter $d_2$ of the second portion 14. The outer diameter $d_2$ of the second portion 14 can include spaces between the filaments, as well, but given the higher pick count and thus tighter weave of the second portion, application of an axial force to the second portion 14 may have minimal to no impact on the diameter $d_2$. In addition, the second portion can have a stronger tendency to maintain its cross-sectional shape and can be less conforming to a different cross-sectional shape of a lumen that it may be in. As shown in FIG. 2D, the suture can also optionally contain a hollow core 18 extending partially or fully therethrough. The core 18 or lumen can be produced from the weave pattern used to form the suture, and the size of the core 18 or lumen can vary as desired. While the sutures in FIGS. 2A-D are depicted as having substantially round cross-sections, it will be understood that the cross-section of the suture can be any shape.

The diameters of the first and second portions can vary, and preferably can be made to correspond with standard USP suture sizes. For example, the first portion can correspond to a standard suture, such as Ethibond® #0 manufactured by ETHICON, Inc., of Somerville, N.J., and the second portion can correspond to available high strength sutures, such as ORTHOCORD® #2 manufactured by DePuy Mitek. In an exemplary embodiment, the sutures can have a diameter in the range of 0.2 mm to 0.7 mm. A person skilled in the art will appreciate that the pick count, the number of fibers, the size of the fibers, etc., can all be selected to provide a suture having a desired diameter along various portions thereof. By way of non-limiting example, a portion of a suture having a pick count of 15 PPI can have a diameter in the range of about 0.25 mm to 0.30 mm, whereas a portion of a suture having a pick count of 60 PPI can have a diameter in the range of about 0.45 mm to 0.65 mm.

The pick count can also affect the flexibility or a bending stiffness of the suture. A lower pick count will result in a reduced bending stiffness and an increased flexibility, as compared to a portion of the suture having a higher pick count. This can allow the suture to be folded and inserted into a small diameter lumen of a suture anchor. In particular, loosely woven fibers can more easily reposition upon bending to allow the suture to deform in shape and/or size. This can result in a reduced cross-sectional profile of the suture, thereby allowing the suture to be inserted into a small diameter lumen. A suture having an increased pick count, on the other hand, will have a higher bending stiffness and thus is less likely to deform when folded. As a result, the suture will assume a larger profile when folded, thus rendering insertion into a smaller diameter anchor more difficult.

Figure 3:
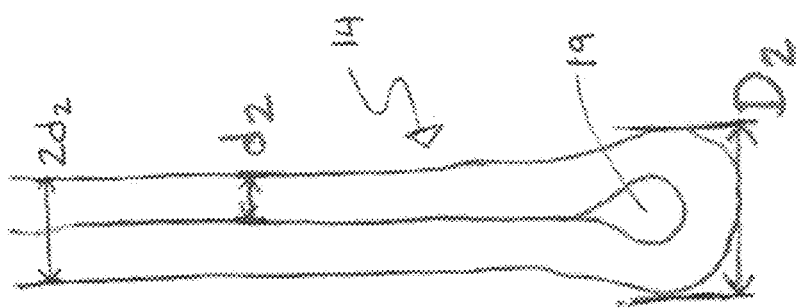
FIG. 3 is a perspective view of the second portion of the suture of FIG. 1 doubled over.

FIG. 3 illustrates the second portion 14 of suture 10, showing the effect of an increased pick count and bending stiffness. A person skilled in the art will appreciate that, while FIG. 3 illustrates a suture having a circular cross-sectional shape, bending of the suture can result in deformation of the cross-sectional shape. The drawings are thus not intended to limit the shape and/or profile of the suture. As shown in FIG. 3, when folding a suture having a higher pick count, the increased bending stiffness of the suture can provide little room for repositioning of the fibers. As a result, the fibers are generally maintained in a relatively tight woven configuration, thus preventing the suture from achieving a true 180 degree bend. This can create a gap 19 at the bend. The greater the bending stiffness of the suture, the greater the size of the gap produced at the bend. The gap can result in a diameter $D_2$ at the bend that is greater than the combined diameter $2d_2$ of two strands of the suture. This can impact the ability to pull the suture into a cannulated suture anchor. By providing a suture having a first portion 12 with a lower pick count and thus lower bending stiffness, the first portion 12 of the suture 10 can deform more easily when bent as compared to the second portion 14 of the suture 10. In particular, the spaces between the fibers of the first portion 12 can allow the fibers to move and reposition relative to one another, thereby allowing the cross-sectional shape of the suture to change. By way of non-limiting example, the cross-sectional shape along a bend in the first portion 12 of the suture 10 can change from a circular shape to an ovular or oblong shape. This will result in a folded portion having a smaller profile, thereby allowing the folded portion to fit into a smaller diameter lumen of a suture anchor, as compared to a folded portion of the second portion 14 of suture 10. A person skilled in the art will appreciate that the diameter or width of the suture at the fold may not necessarily change, but that the ability of the fibers to move due to the loosely woven configuration will facilitate insertion into a small diameter lumen of a suture anchor.

While the suture 10 of FIG. 1 shows a first portion 12 with a lower pick count and a second portion 14 with a higher pick count, various other configurations of suture are possible. The number and length of portions having different pick counts can vary along the length of a suture. In some embodiments, the suture can have more than two distinct portions. For example, a suture can have first, second, third, and fourth sequential portions with alternating pick counts. In particular, the first portion and the third portion can have identical pick counts, and the second portion and the fourth portion can have identical pick counts. Alternatively, in some embodiments, a suture can have more than two different pick counts. For example, the suture can include first, second, third, and fourth portions each having a different pick count. In addition, the pick count can be tailored to change gradually along a length of the suture in almost any desired pattern. Preferably, terminal end portions of a suture have relatively lower pick counts such that the terminal end portions can be more easily threaded into a suture anchor.

As mentioned above, varying pick counts can cause various patterns in the suture. Each pattern can be formed by an uninterrupted series of repeating units. For example, as shown in FIG. 1, the first portion 12 having a first pick count can have a first pattern formed by repeating units 212, and the second portion 14 having a second pick count can have a second pattern formed by repeating units 214. The difference in pattern of the first and second portions 12, 14 is a result of the change in pick count, however, in addition to the pick count, the configuration of the particular weave used to form the suture, and the diameter and color of each filament can also cause variations in the pattern.

The suture 10 can have a length l measured along longitudinal axis L such that it can be threaded through various components, such as a suture anchor. The length of the suture can vary depending on various factors, such as the type of surgical procedure being performed and/or the number of portions with varied pick counts on the suture. For example, the length of the suture can be in the range of about 300 mm to 1000 mm. In some embodiments, the suture can be manufactured as a longer continuous coil that can be cut into resulting separate smaller sutures as needed. The continuous coil of suture can be cut such that the resulting smaller sutures can have a desired pick count along specific portions of the suture. For example, a continuous coil of suture can be cut such that both terminal ends of the resulting smaller sutures can have relatively lower pick counts. The suture can also be used with a suture leader. Non-limiting examples of suture leaders are discussed in U.S. patent application Ser. No. 13/623,290, filed on even date herewith and entitled "Suture Leader," which is incorporated by reference in its entirety.

FIG. 4 illustrates a cut-away view of one exemplary embodiment of a cannulated suture anchor 600 for anchoring tissue to bone. As shown, the suture anchor 600 is in the form of a generally elongate body having proximal and distal ends 600p, 600d with an inner lumen 622 extending therethrough along a longitudinal axis $L_A$. At least one bone-engaging surface feature 624 can be formed on at least a portion of an external surface thereof for engaging bone. The suture anchor 600 can also include a suture-receiving member 626 disposed within and extending across the inner lumen 622 adjacent to the distal end 600d of the suture anchor 600. The suture-receiving member 626 can be adapted to receive one or more sutures therearound such that the suture(s) can extend around the suture-receiving member 626 and trailing ends of the suture(s) can extend through the inner lumen 622 and out of the proximal end 600p of the suture anchor 600.

The body of the suture anchor 600 can have a variety of configurations, shapes, and sizes. In an exemplary embodiment, the anchor 600 is configured to be implanted within a bone tunnel formed in bone, and more preferably it has a size and shape that allows it to be fully engaged through the thickness of the cortical bone. In the illustrated embodiment the body has a generally elongate cylindrical shape with a blunt or rounded distal end 600d to facilitate introduction of the anchor 600 into a bone tunnel. The proximal end 600p of the body can be head-free, as the cannulated configuration of the body can allow a driver to be inserted into the inner lumen to drive the suture anchor into bone. Alternatively, in some embodiments, the suture anchor can have a head portion. As indicated above, the suture anchor 600 can also include one or more bone-engaging surface features 624 formed thereon and adapted to engage bone. While various surface features can be used, such as teeth, ridges, protrusions, etc., in an exemplary embodiment the body can include one or more threads extending therearound.

Figure 5B:
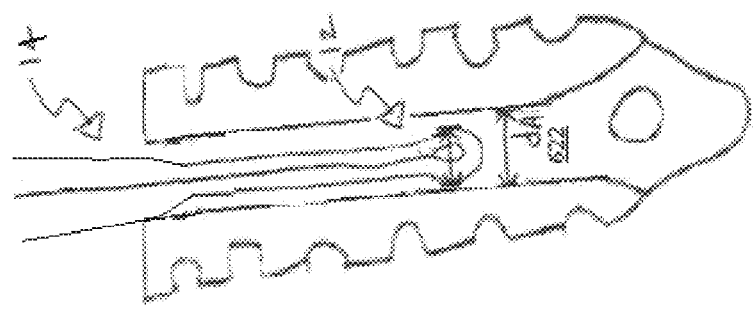
FIG. 5B is a cross-sectional view of the doubled over first portion of the suture partially threaded into the suture anchor of FIG. 4.
Figure 5A:
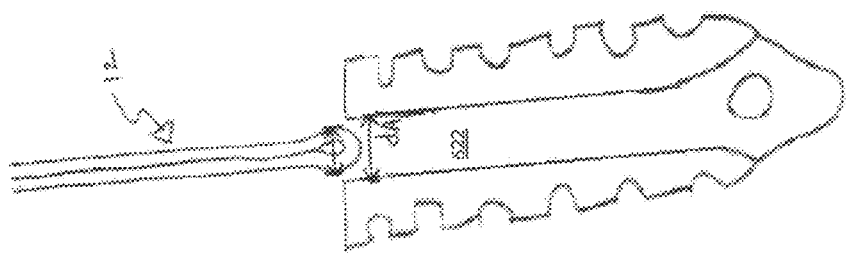
FIG. 5A is a cross-sectional view of a doubled over first portion of the suture of FIG. 1 and the suture anchor of FIG. 4.

The inner lumen 622 of the suture anchor 600 can have a diameter $d_A$ that can vary depending on the type of procedure being performed and the type and number of sutures being used. As previously discussed, the lower pick count of the first portion 12 of the suture 10 can allow the fibers to reposition and the suture to more easily deform along a bend. As shown in FIG. 5A, the lower pick count and greater flexibility will allow the bend in the first portion 12 of the suture 10 to be easily inserted into the inner lumen 622 of the anchor 600. In other words, the bend in the first portion 12 can compress and/or deform more easily so the first portion 12 of the suture 10 can be loaded into the suture anchor 600. Once the first portion 12 of the suture 10 is loaded into the suture anchor 600, it can be pulled further into the inner lumen 622 such that the attached second portion 14 of the suture 10 can follow the first portion 12 into the suture anchor 600, as shown in FIG. 5B. In this way, the second portion 14 can be loaded into the suture anchor 600 without having to bend or fold the suture 10 at the second portion 14. The inner lumen 622 can accommodate four legs of the suture when the suture is fully threaded therethrough, as shown below in FIGS. 8 and 9. In other embodiments, the diameter of the inner lumen can be sized to accommodate multiple strands or various types or sizes of suture, including varying pick counts and bending stiffness.

As previously indicated, the suture anchor 600 can also include a suture-receiving member formed therein. The suture-receiving member 626 can have a variety of configurations, but in an exemplary embodiment it is adapted to seat one or more sutures that extend through the inner lumen 622 of the anchor 600 so as to couple the suture(s) to the anchor. As shown in FIG. 4, the suture-receiving member 626 is in the form of a post that extends transversely across the inner lumen 622 and between opposed inner sidewalls 628, 630 of the suture anchor 600. The angular orientation of the suture-receiving member 626 relative to a longitudinal axis $L_A$ of the inner lumen 622 can vary, but in an exemplary embodiment the suture-receiving member 626 extends substantially perpendicular to the longitudinal axis $L_A$ of the inner lumen 622. The location of the suture-receiving member 626 can also vary, but in an exemplary embodiment the suture-receiving member 626 is positioned at or adjacent to the distal end 600d of the suture anchor 600. In the embodiment shown in FIG. 4 the suture-receiving member 626 is located just proximal to the distal-most end 600d of the suture anchor 600 so as to form a suture-seating groove in the distal-most end 600d of the suture anchor 600. This recessed configuration of the suture-receiving member 626 can allow a suture(s) disposed around the suture-receiving member 626 to sit flush or sub-flush with the distal end 600d of the suture anchor 600 such that the suture(s) will not interfere with insertion of the suture anchor 600 into bone. A person skilled in the art will appreciate that the suture-receiving member can be integrally formed with the suture anchor, i.e., the suture anchor and suture-receiving member can be molded as a single unit or formed from a single piece of material, or the suture-receiving member can be fixedly or removably mated to the suture anchor. Additionally, the suture-receiving member can have other configurations, such as an eyelet (not shown) that can receive the suture therethrough. Non-limiting examples of suture anchors and deploying suture anchors into bone are described in further detail in U.S. application Ser. No. 11/555, 545 entitled "Cannulated Suture Anchor" filed Feb. 1, 2006, now U.S. Pat. No. 8,114,128, U.S. application Ser. No. 11/855,670 entitled "Dual Thread Cannulated Suture Anchor" filed Sep. 14, 2007, U.S. application Ser. No. 10/615,625 entitled "Bioabsorbable Suture Anchor System For Use In Small Joints" filed Jun. 27, 2003, now U.S. Pat. No. 8,133,257, U.S. patent application Ser. No. 13/623,258, filed on even date herewith and entitled "Anti-Backup Suture Anchor," and U.S. patent application Ser. No. 13/623,449, filed on even date herewith and entitled "Self-Cinching Suture Anchors, Systems, and Methods," all of which are hereby incorporated by reference in their entireties.

The devices described above can be used to perform a surgical procedure for attaching tissue to bone, e.g. anterior cruciate ligament (ACL) repair, rotator cuff repair, etc. In an exemplary embodiment, a procedure including implantation of the implant can be a minimally invasive procedure, but as will be appreciated by a person skilled in the art, the implants discussed herein also have application in open surgical instrumentation as well as application in robotic-assisted surgery. Though reference is made to the suture 10, the devices shown are exemplary and the method can be performed with various other sutures.

As one skilled in the art will appreciate, the procedure usually begins by preparing the patient for surgery and making one or more appropriately sized incisions at a desired location. In a minimally invasive procedure, one or more cannulas can be positioned in the incisions to provide access to the surgical site. One skilled in the art will also understand that one or more viewing devices, e.g., scopes, can be placed in one of the incisions to allow medical personnel to view the surgical site from outside the body.

Once the patient is prepared for surgery, a length of suture 10 can be inserted into the patient's body and through tissue to be surgically reattached to bone. When a combination suture and suture leader is used, the leading end of the suture leader can be inserted through the tissue directly using a tool, such as a needle. The leader can be used to pull the suture coupled thereto through the tissue. Alternatively, the suture can be threaded through the tissue and then coupled to the suture leader, e.g., by passing the leading end of the suture into the lumen in the trailing end of the suture leader. One skilled in the art will appreciate that the suture and/or leader can be passed through the tissue using any known surgical technique, such as by mattress and cinch loop methods. With the suture and leader so positioned, a bore, bone hole, or bone tunnel, generally referred to herein as a "bone hole," can be formed in bone of the patient. The bone hole can be pre-formed, such as by using a drill, an awl, a punch instrument, etc., as will be appreciated by a person skilled in the art. Alternatively, the bone hole can be formed simultaneously with advancement of a suture anchor into the bone and simultaneously with threadable engagement of the anchor therewith, such as by using a self-awling or self-tapping driver and/or self-awling or self-tapping anchor. The bone hole can extend fully through cortical bone to allow the suture anchor to be fully engaged through the thickness of the cortical bone. The bone tunnel can also extend into cancellous bone located underneath the cortical bone. The suture anchor can be deployed in the bone hole before or after suture leader is threaded or loaded onto the suture anchor. With the suture and/or leader(s) threaded through tissue, the terminal ends can extend outside of the body. The suture and the leader can be threaded onto the anchor, either before or after the anchor is implanted in bone.

Figure 6:
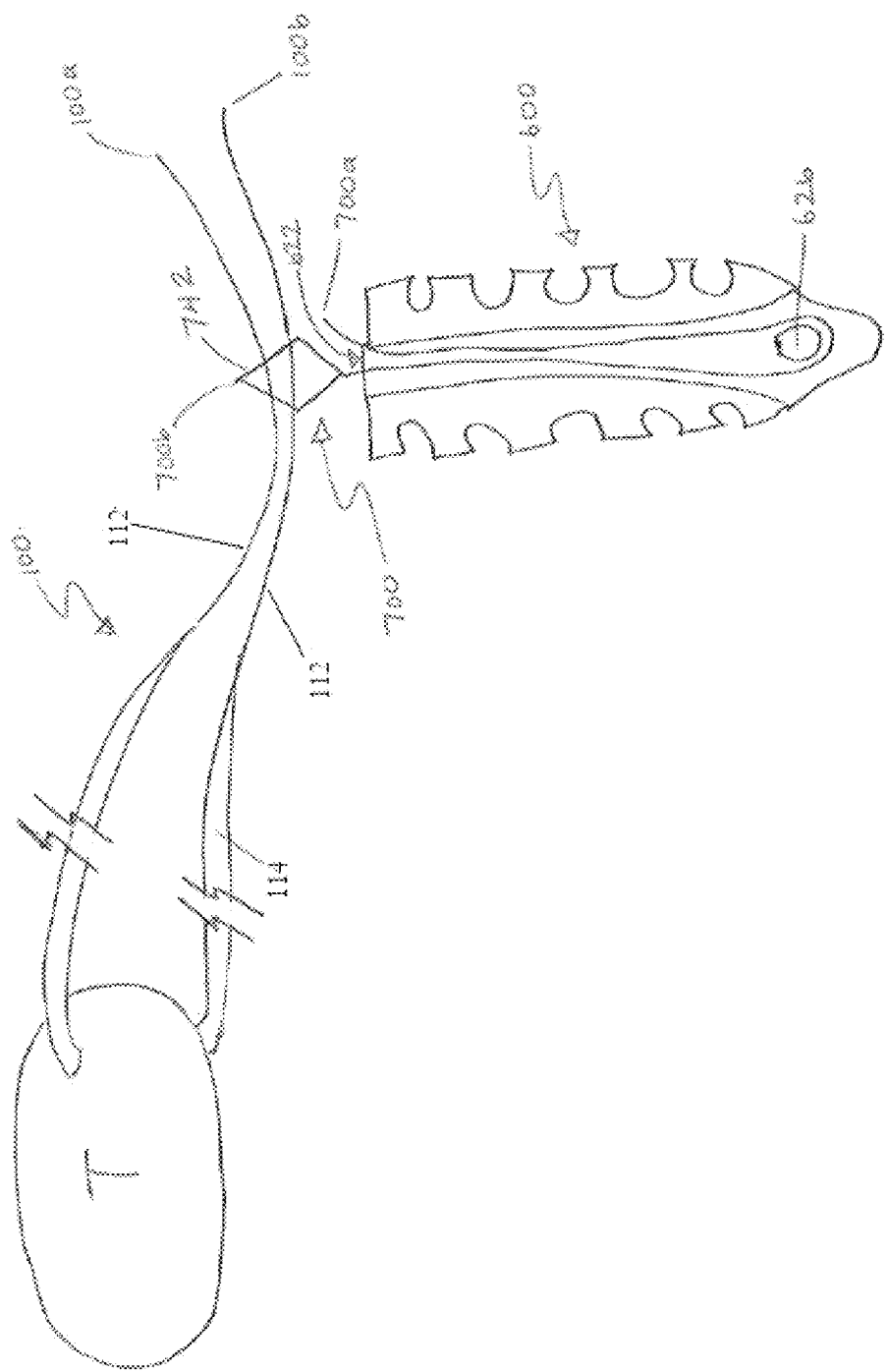
FIG. 6 is a cross-sectional view of one suture threaded through tissue and into a threader loop extending from the suture anchor of FIG. 4.
Figure 7:
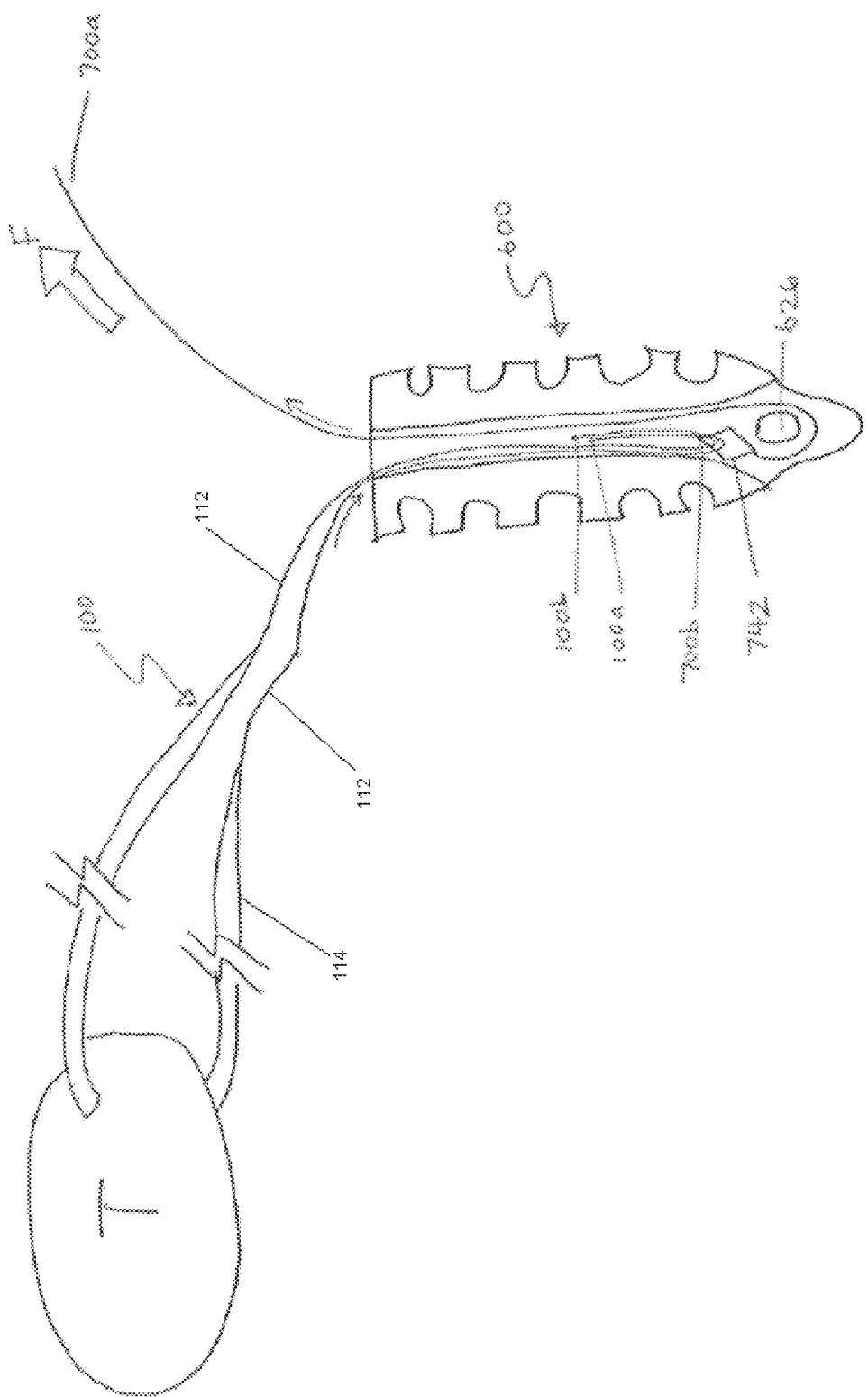
FIG. 7 is a cross-sectional view of the suture of FIG. 6 partially threaded through the suture anchor.

With the suture extending through or around tissue, the trailing ends can extend outside of the body and can be manipulated by a user. In one embodiment, the suture can be threaded onto the anchor while the anchor is positioned outside of the patient's body. The suture can be threaded through the anchor in various ways and using various tools known in the art, such as a threader loop. For example, as shown in FIG. 6, a suture 100 having a first portion 112 with a lower pick count a second portion 114 with a greater pick count can be threaded through tissue T. The first portion 112 can include opposite end portions of the suture 100, which include trailing ends 100a, 100b. The suture 100 can then be threaded through a loop portion 742 located on a trailing end 700b of a threader loop 700 prior to threading the suture 100 through the anchor 600. Preferably, the first portion 112 is threaded through the threader loop 700 because the lower pick count and lower bending stiffness can allow it to deform and/or compress at the bend when bent around the loop portion 742 of the threader loop 700, as shown in FIG. 7, making the first portion 112 easier to thread into the suture anchor 600 than the second portion 114 or a standard high strength suture. When the threader loop 700 or other threading tool is used, the threader loop 700 can optionally be pre-disposed within the lumen/cannulated portion 622 of the anchor 600, as shown in FIG. 6. The threader loop 700 can be wrapped around the suture-receiving member 626 and a leading end 700a of the threader loop 700 can exit from the same opening of the suture anchor 600 that it entered such that both the leading and trailing ends 700a, 700b of the threader loop 700 extend from a proximal end of the suture anchor 600, as shown in FIG. 6.

Figure 8:
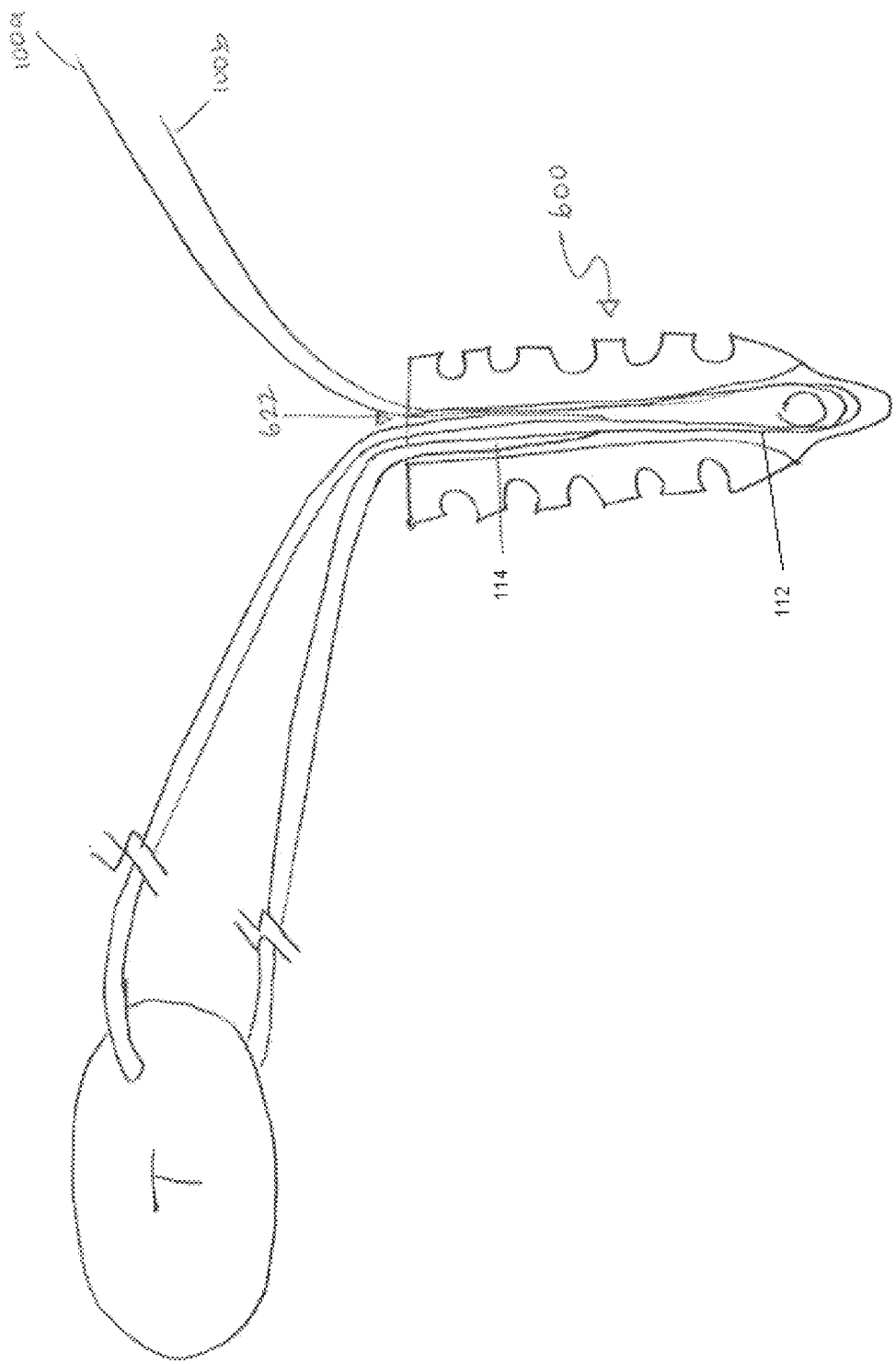
FIG. 8 is a cross-sectional view of the suture of FIG. 7 fully threaded through the suture anchor.
Figure 9B:
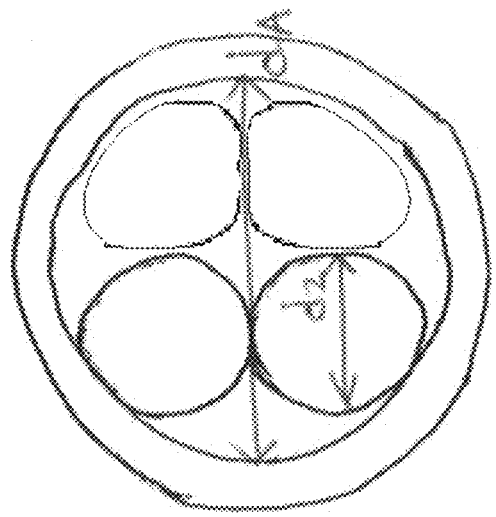
FIG. 9B is an alternative cross-sectional top view of the suture of FIG. 8 threaded through the anchor.
Figure 9A:
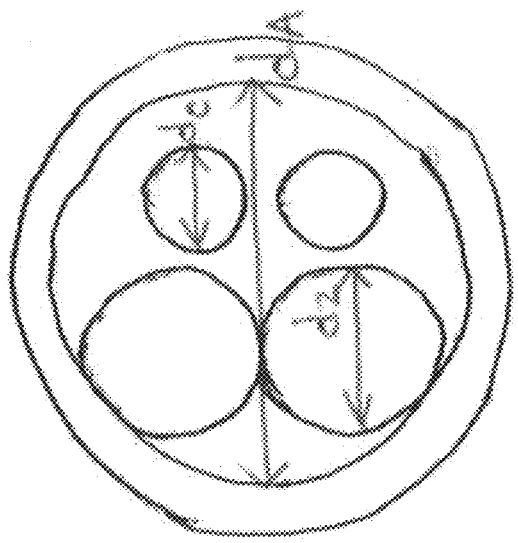
FIG. 9A is a cross-sectional top view of the suture of FIG. 8 threaded through the anchor.

The leading end 700a of the threader loop 700 can be pulled proximally with a force F such that the trailing end 700b is pulled distally into the suture anchor 600 with the first portion 112 of the suture 100 folded around the loop portion 742, as shown in FIG. 7. As the leading end 700a of the threader 700 is further pulled proximally, the trailing end 700b, and thus the attached suture 100, are pulled around the suture-receiving member 626 and then pulled proximally through the suture anchor 600. The axial force on the suture produced by the pulling of the threader loop can cause a diameter of the first portion of the suture to collapse and/or deform such that it conforms to the confines of the lumen of the anchor. The threader loop 742 can be further pulled proximally such that the trailing end 700b exits the proximal end of the suture anchor 600, pulling the trailing ends 100a, 100b and the first portion 112 of the suture with it, as shown in FIG. 8. The first portion 112 of the suture 100 can be pulled such that the second portion 114 of the suture 100 is partially threaded through the suture anchor 600, as shown in FIG. 8, or alternatively, the first portion can be pulled such that the second portion is either not at all threaded or fully threaded through the suture anchor. In other embodiments, the threader can pass through the distal end of the suture anchor, pulling the suture thereafter. In these embodiments, the suture can be left extending from the distal end of the anchor, or it can be threaded back through the anchor in a distal to proximal direction. The first portion 112 of the suture can have a length such that it can extend substantially through the inner lumen 622 of the anchor 600, as shown, or in other embodiments the first portion can extend partially through the lumen 622. FIG. 9A shows a cross-section of the top view of the suture anchor 600 once the suture 100 has been fully threaded therethrough. FIG. 9B shows an alternative cross-section of the top view of the suture anchor 600 once the suture 100 has been fully threaded therethrough such that the cross-sectional shape of the first portion 112 deformed. While FIGS. 9A and 9B show the suture 100 fully threaded through the suture anchor such that each of the first portion 112 and the second portion 114 are partially threaded through the suture anchor 600, the suture can alternatively be fully threaded through the anchor such that either the first portion 112 is entirely threaded through the suture anchor or the second portion 114 is entirely threaded through the suture anchor.

With the suture 100 threaded through the suture anchor 600, the suture anchor 600 can be deployed into the bone using various techniques. For example, the suture anchor 600 can be positioned on a distal end of a driver (not shown), and the driver can be rotated to force the suture anchor 600 through the bone, such as through the bone tunnel previously described. The suture 100 can be tensioned to draw the tissue toward the suture anchor 600 either prior to, during, or subsequent to driving the suture anchor 600 into the bone. When the suture anchor 600 is fully seated in the bone, it can extend at least through cortical bone or through cortical bone and cancellous bone. After the suture 100 is tensioned to pull the tissue toward the bone, trailing ends 100a, 100b of the suture 100 can be tied off or otherwise secured to maintain contact between the tissue and the bone. Various methods can be used to secure the suture, for example, a single or multiple knots, a self-knotting suture, or a knotting element, as will be appreciated by one of skill in the art. For example, the trailing ends 100a, 100b of the suture 100 can be knotted together such that tissue T attached to the suture 100 can be securely anchored to the suture anchor 600, and thus to the bone.

As previously indicated, the suture anchors disclosed herein can be configured for use with one or more sutures. The particular quantity of sutures used with a suture anchor can depend on the size of the suture anchor, and in particular on the diameter of the inner lumen of the suture anchor.

Any combination of the devices described above can be provided in a surgical kit. For example, the kit can include one or more sutures having varied pick counts as described above. The kit can include one or more suture anchors of various shapes and sizes, depending on the type of procedure to be performed and the types of sutures included. Alternatively, the kit can include suture anchors of similar shapes and/or sizes that each have inner cannulas having different diameters. The kit can also include a threader tab or any other threading tools.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical kit, comprising:
   a biocompatible elongate weave of longitudinal fibers having a first length with a first pick count defined by the longitudinal fibers and a second length with a second pick count defined by the longitudinal fibers that is greater than the first pick count, wherein the longitudinal fibers are continuously woven together throughout the first and second lengths, and wherein a cross-section of the first length is configured to deform when a force is applied thereto; and
   a cannulated anchor having an inner lumen configured to receive the weave of longitudinal fibers.

2. The surgical kit of claim 1, wherein the inner lumen is configured to receive a doubled over portion of the first length of the weave of longitudinal fibers.

3. The surgical kit of claim 1, further comprising a threader tab configured to pull the weave of longitudinal fibers into the inner lumen of the cannulated anchor.

4. The surgical kit of claim 1, further comprising at least one additional biocompatible elongate weave of fibers.

5. The surgical kit of claim 1, wherein the first length has a resting outer diameter that is greater than or equal to an outer diameter of the second length, and the first length is configured to collapse in diameter when a force is applied thereto.

6. The surgical kit of claim 5, wherein the collapsed outer diameter of the first length is less than the outer diameter of the second length.

7. The surgical kit of claim 1, wherein the second length has a bending stiffness that is greater than a bending stiffness of the first length.

8. The surgical kit of claim 1, wherein the elongate weave of the longitudinal fibers includes a hollow lumen extending at least partially therethrough.

9. The surgical kit of claim 1, wherein the weave of longitudinal fibers has a third length with the first pick count, and the weave of longitudinal fibers has a fourth length with the second pick count, the first, second, third, and fourth lengths being sequentially located along a longitudinal length of the weave of longitudinal fibers.

10. The surgical kit of claim 1, wherein the weave of longitudinal fibers has a third length with a third pick count, the weave of longitudinal fibers has a fourth length with a fourth pick count, the first, second, third, and fourth pick counts being different from one another, and the first, second, third, and fourth lengths being sequentially located along a longitudinal length of the weave of longitudinal fibers.

11. The surgical kit of claim 1, wherein the first length is disposed within the inner lumen and the second length is positioned outside the inner lumen.

12. A surgical kit, comprising:
a biocompatible suture including continuous fibers extending between first and second terminal ends of the suture that define a longitudinal length of the suture, the continuous fibers in a first portion of the longitudinal length having a first pick count, and the continuous fibers in a second portion of the longitudinal length having a second pick count that is greater than the first pick count; and
a cannulated anchor having an inner lumen extending between proximal and distal ends thereof, the anchor having a suture-receiving member disposed within the inner lumen, the suture-receiving member being configured to have a portion of the suture received therearound such that a first length of the suture extends through the inner lumen and a second length of the suture extends out the proximal end of the anchor.

13. The surgical kit of claim 12, wherein the first portion defines a first pattern of the continuous fibers and the second portion defines a second pattern of the continuous fibers that differs from the first pattern.

14. The surgical kit of claim 13, wherein the first and second patterns each comprise an uninterrupted series of repeating units.

15. The surgical kit of claim 14, wherein the repeating unit on the first pattern has a length that is greater than a length of the repeating unit on the second pattern.

16. The surgical kit of claim 12, wherein the continuous fibers in a third portion of the longitudinal length has the first pick count, and the continuous fibers in a fourth portion of the longitudinal length has the second pick count, the first, second, third, and fourth portions being sequentially located along the longitudinal length of the suture.

17. The surgical kit of claim 12, wherein the continuous fibers in a third portion of the longitudinal length has a third pick count that is different from the first and second pick counts, the continuous fibers in a fourth portion of the longitudinal length has a fourth pick count that is different from the first, second, and third pick counts, the first, second, third, and fourth portions being sequentially located along the longitudinal length of the suture.

18. A surgical kit, comprising:
a biocompatible elongate weave of fibers having a longitudinal length, a first portion of the longitudinal length having all of the fibers cross a first number of times for every inch of length of the first portion, a second portion of the longitudinal length having all of the fibers cross a second number of times for every inch of length of the second portion, the second number of times being greater than the first number of times, wherein a cross-section of the first portion is configured to deform when a force is applied thereto; and
a cannulated anchor having an inner lumen configured to receive the weave of fibers.

19. The kit of claim 18, wherein the second portion has a bending stiffness that is greater than a bending stiffness of the first portion.

* * * * *